US00PP07933P

United States Patent [19]

Hanes

[11] Patent Number: Plant 7,933

[45] Date of Patent: Aug. 11, 1992

[54] GERANIUM NAMED AMERICANA SALMON

[75] Inventor: Mitchell Hanes, Morgan Hill, Calif.

[73] Assignee: Goldsmith Seeds, Inc., Gilroy, Calif.

[21] Appl. No.: 645,800

[22] Filed: Jan. 25, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

The new and distinct Geranium cultivar particularly distinguished by its salmon colored semi-double flowers on large umbels, the plant being fast-rooting and having a vigorous bush-like growth habit and foliage with light zonation.

2 Drawing Sheets

BACKGROUND OF THE NEW PLANT

The present invention comprises a new and distinct cultivar of Geranium, botanically known as *Pelargonium hortorum* Bailey, and hereinafter referred to by the cultivar name Americana Salmon. The new cultivar is propagated from a seedling resulting from the crossing, as the seed parent, an F2 of 'Blues' (U.S. Plant Pat. No. 5,373) with the pollen parent Pink Camellia (unpatented).

Americana Salmon is a product of a planned breeding program intended to create new Geranium cultivars with salmon flower color, semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawings of which

DESCRIPTION OF THE NEW CULTIVAR

Figure 1:
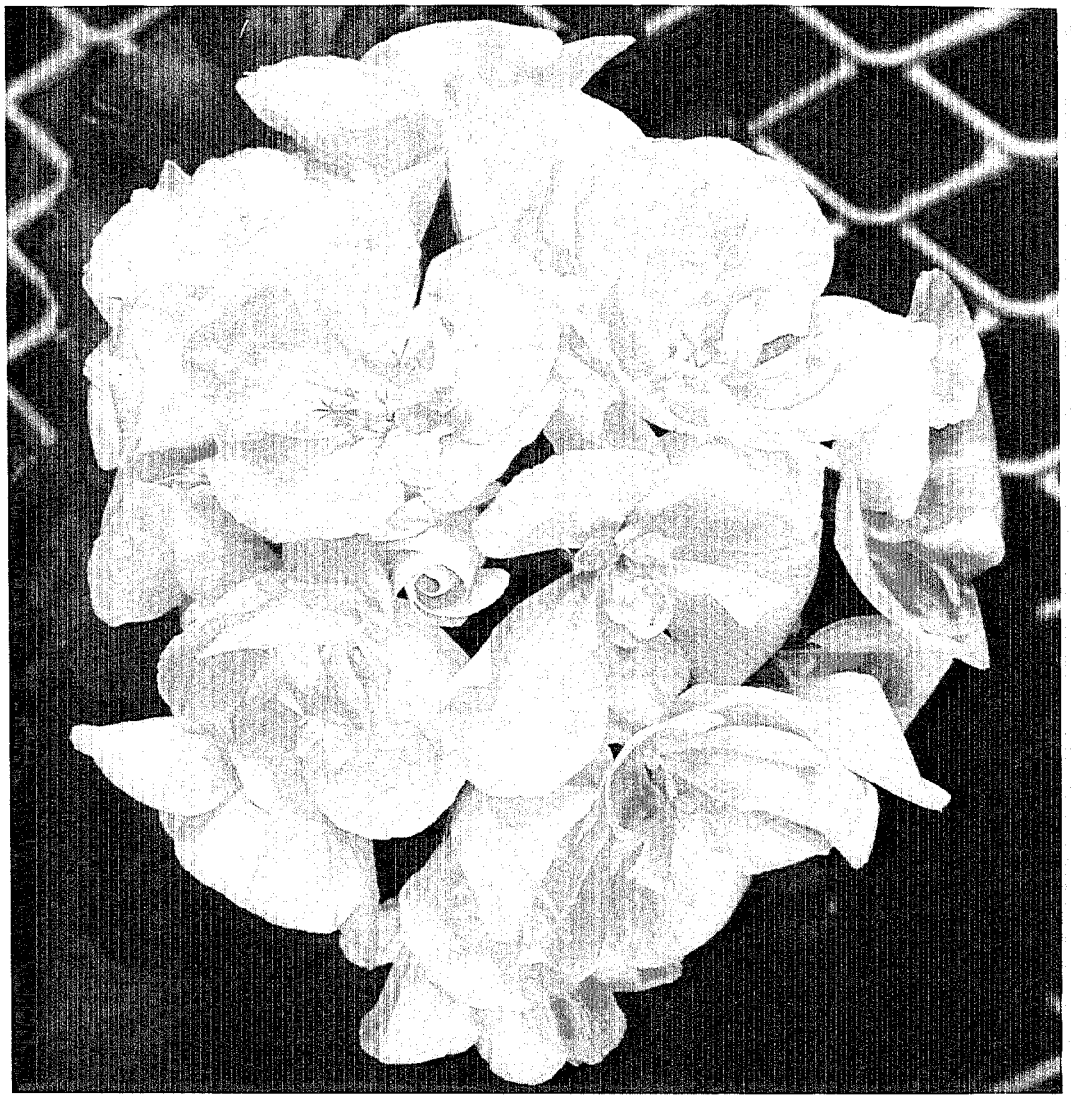
FIG. 1 shows a face view of a blooming umbel of the plant in full color, the colors shown being as true as can be reasonably obtained by conventional photographic procedures.
Figure 2:
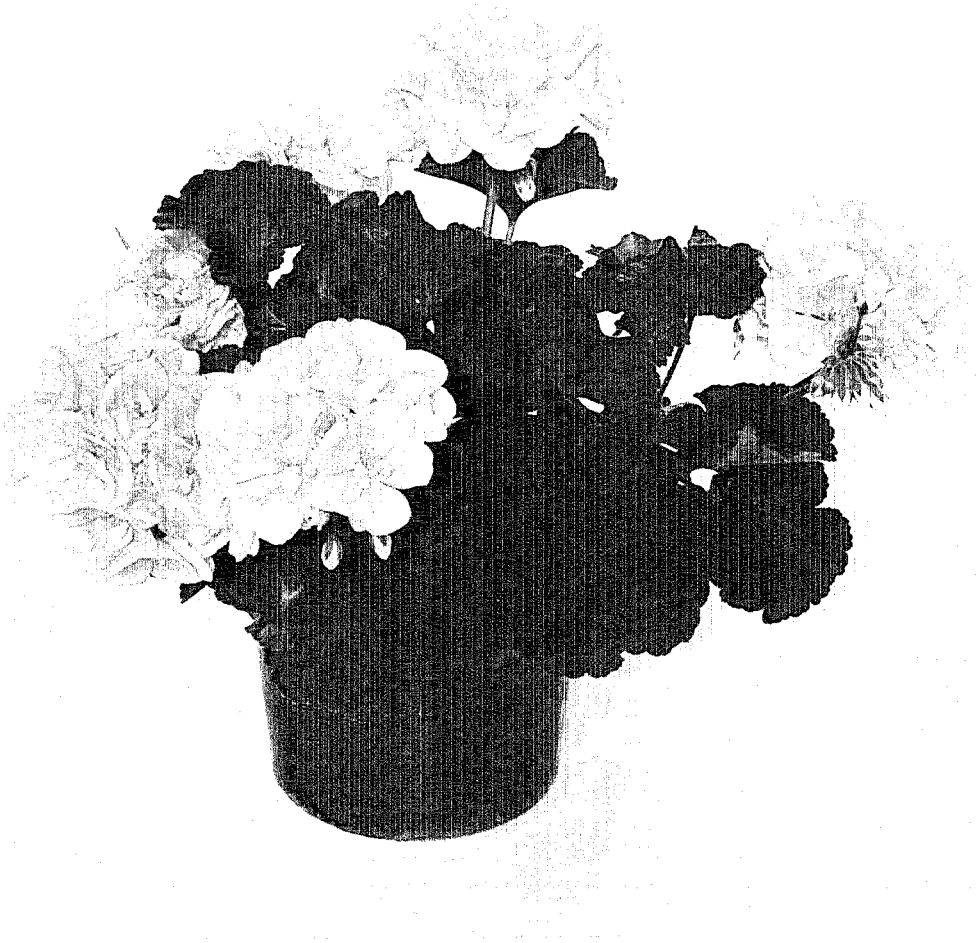
FIG. 2 is a view of a potted plant of this new variety intended only to illustrate its growth habit.

The following detailed description set forth the distinctive characteristics of the new plant and the data which defines these characteristics were collected from asexual reproductions carried out in Gilroy, Calif. The plant history was taken on six week plants, blossomed under natural light in a greenhouse and color readings were taken indoors under 100 foot candles of cool, white fluorescent light. Color references are primarily to The R.H.S. Colour Chart of The Royal Horticultural Society of London (R.H.S.).

THE PLANT

Classification: *Pelargonium hortorum* Bailey.

*Commercial.*—Zonal geranium.

Form: Vigorous bush.

Height: 12 to 16 cm., as a 5½ inch pot plant, excluding blooms.

Growth: Upright, somewhat spreading habit, and very fast rooting.

Strength: Very sturdy and not susceptible to wind or rain damage. Good shipping ability as rooted or unrooted cuttings.

Foliage: Abundant quantity.

*Leaves:*

*Size.*—Diameter about 11 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 6 to 7 cm. long.

*Color.*—Upper side: Green with light zonation on the outside edge. Underside: Lighter green color without zonation. Ribs and veins not prominently different from upper surface.

Petioles: About 5 to 6.0 cm. in length.

THE BUD

Size:

*Diameter.*—About 7 mm.

*Length.*—About 1.5 cm to 2.0 cm. at time of bud opening.

Shape: Pointed ovoid.

Color: Of petals when sepals first divide, R.H.S. 159-D.

Sepals: Five in number, flat behind petals. Pointed linear lanceolate, R.H.S. 143-D in an open flower.

THE FLOWER

Blooming habit: Continuous throughout the year.

Size: Approximately 4.5 cm. diameter, 1 cm. deep, irregularly radially symmetrical.

Form: Cup-shaped when bloom first opens, later flattening the shallow cup shape with maturity.

Petals: Five imbricate outer petals, 2.3–2.5 cm. wide and approximately 2.2 cm. long. Three to eight inner smaller petaloids of varying shape. Both the outer petals and inner petaloids are salmon, R.H.S. 47-C with color most intense near the claw and fading lighter to the outer margin. Veins slightly darker than interveinal regions. Color changing little with age. Underside of petals lighter. Petals and petaloids soft and satiny.

Pedicel: Approximately 1.6 cm. in length.

Persistence: Nonshattering flower.

INFLORESCENSE

Type: An umbel composed of approximately 35 flowers, erect or laterally ascending, the diameter of the umbel being approximately 9–11 cm.

Peduncle: Approximately 10–15 cm. in length, mostly 14 cm.; green with occasional reddish tint on the side of the stem facing the sun.

REPRODUCTIVE ORGANS

Stamens:

*Anthers.*—Six to eight positioned below the mature stigma, dull red prior to anthesis.

*Filaments.*—White near base and mid length, graduating to dull red near anther.

*Pollen.*—Orange in color.

Pistil:

*Number.*—One.

*Length.*—Approximately 5 mm.

*Stigma.*—Five linear lobes of near equal length, curling back toward ovary, purplish-red.

*Style.*—

*Length.*—About 2–2.5 mm., color: purplish red.

*Ovaries.*—At anthesis, densely pubescent with white hairs, oblong. Green drying to a light brown at maturity.

Fruit: Partially fertile.

I claim:

1. A new and distinct Geranium cultivar substantially as herein shown and described, characterized by its green foliage with light zonation, salmon colored, semi-double flowers on large umbels; the plant being fast-rooting and having a vigorous bush-like growth habit.

* * * * *